(12) United States Patent
Yaniv

(10) Patent No.: US 7,611,906 B2
(45) Date of Patent: Nov. 3, 2009

(54) FUNCTIONALIZED CARBON NANOTUBES

(75) Inventor: Zvi Yaniv, Austin, TX (US)

(73) Assignee: Applied Nanotech Holdings, Inc., Austin, TX (US)

( * ) Notice: Subject to any disclaimer, the term of this patent is extended or adjusted under 35 U.S.C. 154(b) by 0 days.

(21) Appl. No.: 11/625,653

(22) Filed: Jan. 22, 2007

(65) Prior Publication Data
US 2007/0172851 A1 Jul. 26, 2007

Related U.S. Application Data

(60) Provisional application No. 60/761,113, filed on Jan. 23, 2006.

(51) Int. Cl.
G01N 33/551 (2006.01)
(52) U.S. Cl. .................. 436/524; 977/702; 977/707; 977/746; 435/283.1
(58) Field of Classification Search .............. 428/292.1; 252/500; 423/447; 977/702; 436/524
See application file for complete search history.

(56) References Cited

U.S. PATENT DOCUMENTS

| 2003/0098488 | A1 | 5/2003 | O'Keeffe et al. |
| 2003/0148086 | A1 | 8/2003 | Pfefferle et al. |
| 2003/0148562 | A1 | 8/2003 | Luyken et al. |
| 2003/0186522 | A1 | 10/2003 | Duan et al. |
| 2003/0218224 | A1* | 11/2003 | Schlaf et al. ................. 257/414 |
| 2004/0213910 | A1* | 10/2004 | Cai et al. ..................... 427/299 |
| 2004/0235016 | A1* | 11/2004 | Hamers et al. .................. 435/6 |
| 2004/0238887 | A1 | 12/2004 | Nihey |
| 2005/0184294 | A1* | 8/2005 | Zhang .......................... 257/77 |
| 2006/0204738 | A1* | 9/2006 | Dubrow et al. ............ 428/292.1 |

OTHER PUBLICATIONS

K. Keren, et al. "DNA-Templated Carbon Nanotube Field-Effect Transistor," Science, vol. 302, pp. 1380-1382; Nov. 21, 2003.
K. Keren, et al. "Sequence-Specific Molecular Lithography on Single DNA Molecules," Science, vol. 297, pp. 72-75; Jul. 5, 2002.
J. Bonard, et al. "Degradation and Failure of Carbon Nanotube Field Emitters," Physical Review, vol. B 67, pp. 115406-1-115406-10; Mar. 17, 2003.
DNA'a Application in Nanoscale Device [online], [Retrieved from the internet Apr. 19, 2006]. Retrieved from the internet: <URL: http://www.nanologoy.uste.edu.cn/Chinese/service/Student%20presentation/dna_app.pdf>; May 1, 2004.

(Continued)

Primary Examiner—N Yang
(74) Attorney, Agent, or Firm—Kelly K. Kordzik; Fish & Richardson P.C.

(57) ABSTRACT

Carbon nanotubes are grown on a first substrate. The CNTs grown on the first substrate are immersed in a biological solution at a predetermined depth to functionalize ends of the CNTs with a biological molecule. The functionalized CNTs are harvested from the first substrate. A second substrate is functionalized with a complementary biological modification, which is a complementary binding partner to the biological molecule functionalized to the ends of the CNTs. The functionalized CNTs are attached to the second substrate by way of the complementary binding partner.

16 Claims, 4 Drawing Sheets

OTHER PUBLICATIONS

DNA Used to Create Self-Assembling Nano Transistor. Nano Techwire.com, [online] [retrieved Jan. 22, 2007]. [Retrieved from the internet] <URL: http://nanotechwire.com/news.asp?nid=537>; Nov. 25, 2003.

Self-Assembly of Molecular Scale Electronics by DNA Molecules and Related Proteins [online], [Retrieved from the internet Apr. 19, 2006] <URL: http://www.lancs.ac.uk/users/esqn/nanoelectronics/presentations/sivan.pdf>; Publication date unknown.

M. Sousa, et al. "Patterning Lyotropic Liquid Crystals as Precursors for Carbon Nanotube Arrays," *Applied Physics Letter*, vol. 87, pp. 173115-1-173115-3; Oct. 20, 2005.

M. Jung, et al. "Electrical and Field-Emission Properties of Chemically Anchored Single-Walled Carbon Nanotube Patterns," Applied Physics Letter, vol. 87, pp. 013114-1-013114-3; Jul. 1, 2005.

A. Musatov, et al. "Field Emission From Carbon Layers Containing Very Long and Sparse Nanotubes/Nanofilaments," Applied Physics Letter, vol. 87, pp. 181919-1-181919-3; Oct. 28, 2005.

Notification of Transmittal of the International Search Report and the Written Opinion of the International Searching Authority for PCT/US07/60881 filed Jan. 23, 2007 (12 pages). Mailed Sep. 12, 2008 from the PCT International Searching Authority.

\* cited by examiner

FUNCTIONALIZED CARBON NANOTUBES

This application claims priority to U.S. provisional patent application Ser. No. 60/761,113, which is incorporated by reference herein.

TECHNICAL FIELD

The present invention relates in general to carbon nanotubes, and in particular, to the functionalization of carbon nanotubes.

BACKGROUND INFORMATION

Carbon Nanotubes (CNTs) are used in their electron emission mode for many applications. In some of these applications, the CNTs are deposited on a substrate, resulting in the field emission cathode. In their electron emission mode, the CNTs are operated at high fields, and their adherence to the cathode substrate is very important. There are mainly two methods for CNTs to be deposited on cathodes. One is direct deposition by chemical vapor deposition (CVD) on the substrate that requires, in general, high temperatures, and as a result, is not compatible with low cost substrates. The other method is the use of CNTs that are already manufactured, in which case, in order to secure the adherence of the CNTs to the cathode substrate, inks and pastes, etc., may be utilized. Although these inks and pastes assist in adherence of these types of CNTs to the substrate, the emission characteristics of the carbon nanotubes are changed, and an activation process may be required to free the carbon nanotubes from the adhesion layer constituted of inks or pastes. These inks or pastes are based on a mixture of organic and inorganic materials. In general, the CNTs in inks and pastes have a higher threshold voltage, their electron emission is not uniform, and as a result, it is very difficult to produce high quality CNT televisions. Furthermore, the organic materials may disturb the high vacuum necessary for electron emission operation.

DETAILED DESCRIPTION

Figure 1:
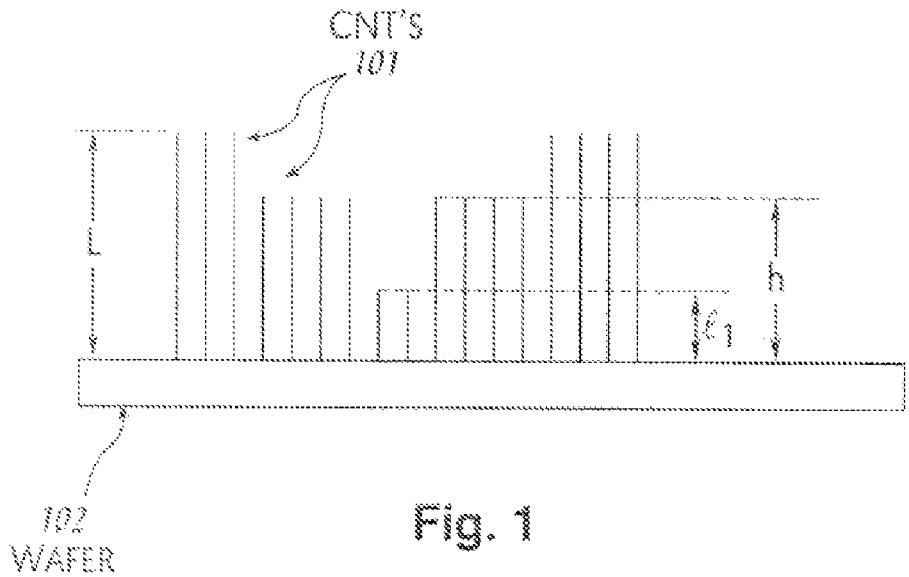
FIG. 1 illustrates carbon nanotubes grown on a substrate and having different lengths.

In the following description, numerous specific details are set forth such as specific cathode materials, etc. to provide a thorough understanding of the present invention. However, it will be obvious to those skilled in the art that the present invention may be practiced without such specific details. In other instances, well-known circuits have been shown in block diagram form in order not to obscure the present invention in unnecessary detail. For the most part, details concerning timing considerations and the like have been omitted inasmuch as such details are not necessary to obtain a complete understanding of the present invention and are within the skills of persons of ordinary skill in the relevant art.

Refer now to the drawings wherein depicted elements are not necessarily shown to scale and wherein like or similar elements are designated by the same reference numeral through the several views.

It has been demonstrated that CNTs align in an electric field toward an anode when a high electric field is applied. As a result, the theories that CNTs must be previously aligned are not adequate.

Furthermore, it has been demonstrated that electron emission uniformity is improved if carbon nanotubes are substantially equal in length such that no hot spot of higher electric fields are created destroying the uniformity.

Although, an embodiment of the present invention is described around one example of making cathodes for CNT televisions, this invention is not limited to these types of devices. In addition to making CNT TV cathodes, embodiments of the present invention are applicable to other bodies, antibodies or chemicals that have specific abilities to bind between them or bind in a localized fashion along the length of the CNT. By functionalizing the CNTs on specific locations along the axis of the CNT, a multiple of optoelectronic devices can be realized solving some of the processing and reliability issues created by the use of usual types of microelectronic processes.

At least one embodiment of the present invention uses precise location functionalization of CNTs over the length of the CNTs. For example, in some cases one would like to functionalize only a small portion in one of the ends of a CNT or both ends. In other situations, one may want to functionalize the CNT in the middle part of its length. It, for example, one were able to functionalize only one end of the CNT, and not its entire length, and then find a way to anchor this localized functionalized CNT on the substrate, a situation is achieved where a multitude of CNTs are all anchored in one end to the substrate, having the majority of their length available to direct themselves toward the anode when an electric field is applied.

This method in this case solves the issue of activation, the use of inks or pastes (improving the vacuum necessary in the device), and also can be utilized to screen the very long or very short CNTs with respect to the average desired length. Furthermore, it is easier to control the density of carbon nanotubes on the substrate.

As an example, the following describes how a CNT cathode may be used for electron emission in a CNT TV or other products. These cathodes may be made such that the CNTs are strongly attached to the substrate only at one of their ends and when they bend in the field they are substantially the same length, achieving in such a way a very uniform electron emission pattern, and as a result light emission uniformity from the anode.

Referring to FIG. 1, a process of the present invention begins with CNTs 101 grown on a wafer 102 by one of various methods known in the industry. For example, perpendicular CNTs 101 may be grown by a CVD process on a wafer 102 such that the CNTs 101 are parallel to each other having more or less an average height, h, with CNTs 101 longer and shorter than h. Assume that the maximum length is L and the minimum length is l.

Figure 2:
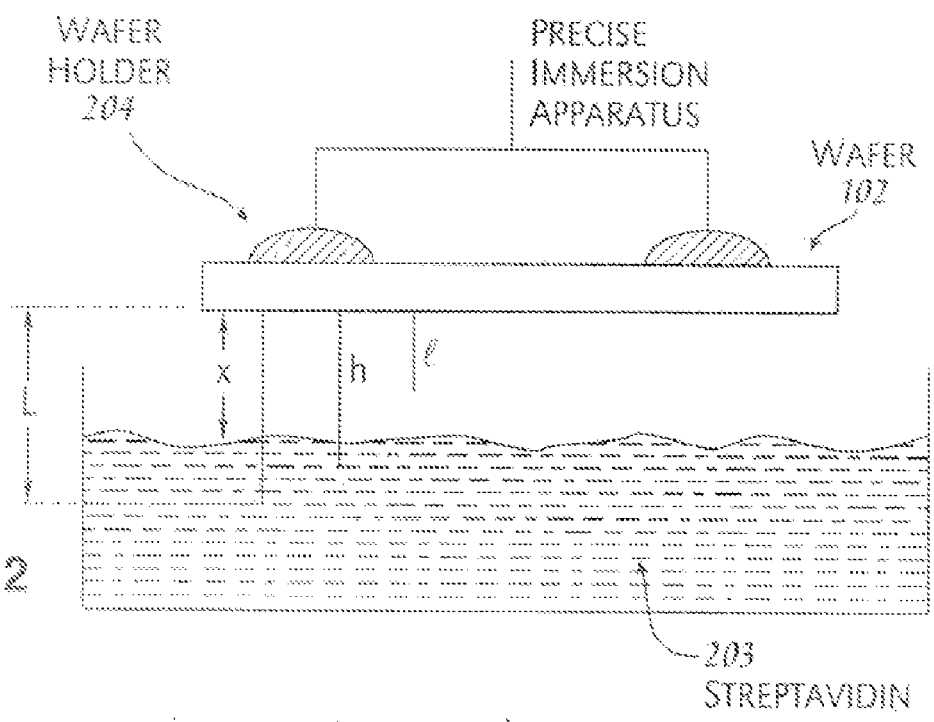
FIG. 2 illustrates immersion of the CNTs in streptavidin.
Figure 3:
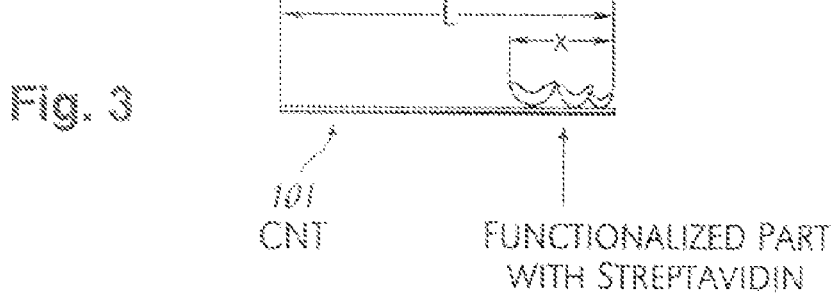
FIG. 3 illustrates a functionalized CNT.

The wafer 102 with the CNTs 101 grown on it may be immersed into a functionalizing agent 203 with nanometric precision through a precise immersion apparatus, and wafer holder 204 as shown in FIG. 2. Because it may be desired to have the height of the CNTs 101 on the final cathode to be approximately h in the electric field, the wafer 102 may be immersed such that only the ends of the CNTs 101 having a length h or greater will be immersed in the functionalizing agent 203. As an example of a functionalizing agent 203, streptavidin may be used, which has very specific binding properties to another chemical, biotin. Referring to FIG. 3, streptavidin homogeneously covers the immersed parts of the CNTs by adsorption as was indicated by fluorescence microscopy (see, Braun et al., *DNA-Templated Carbon Nanotube Field-Effect Transistor*, Science, Vol. 302, Nov. 21, 2003). After the functionalization as described above, the CNTs 101 on the wafer 102 are harvested by controlled chemical etching (using piranha and ammonium persulfate solutions), laser, microtome or other method.

Figure 4:
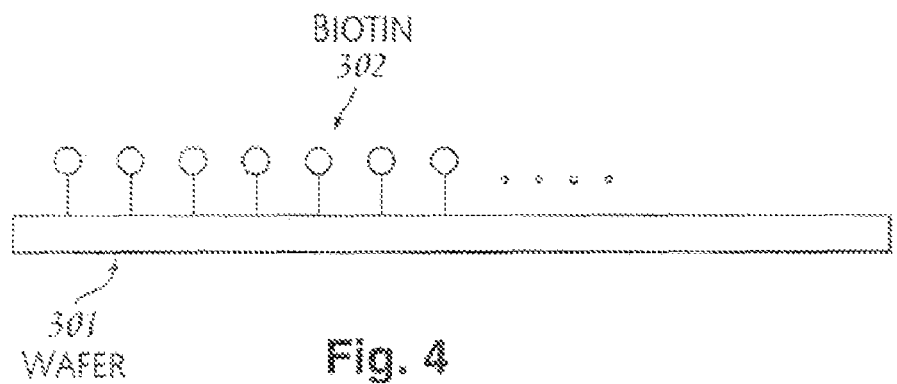
FIG. 4 illustrates a substrate coated with biotin.
Figure 5:
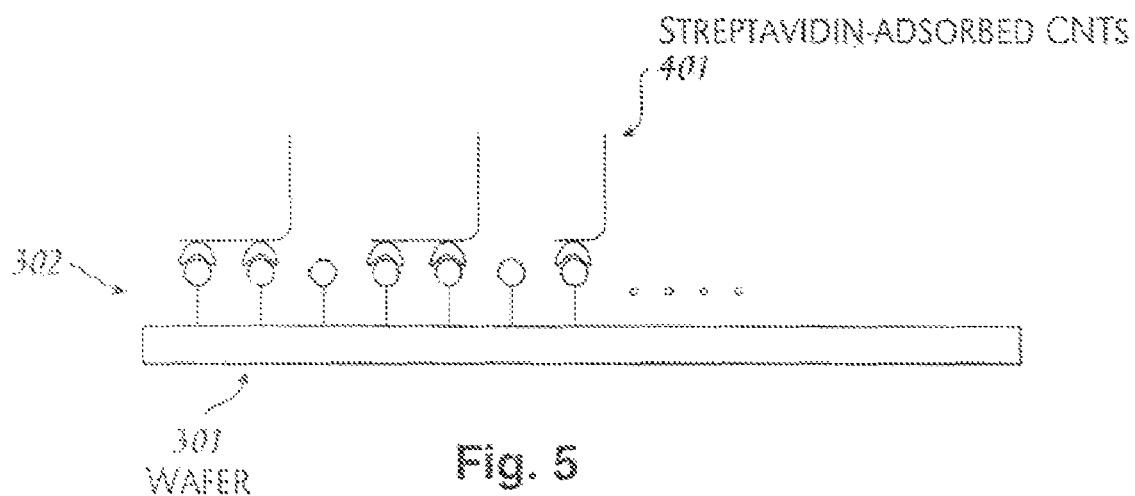
FIG. 5 illustrates streptavidin-absorbed CNTs having a high affinity for biotin.

Referring to FIG. 4, a substrate 301 (e.g., glass), which will be the base of the cathode, is coated with a material that has high affinity to streptavidin (in the present example, biotin 302 may be used). These coatings can be covalently attached to the substrate surface through thiol-, sulfhydryl- or amine-based surface modifications. In one example, a silanized glass or indium-tin oxide (ITO) surface presenting amine groups can be reacted with the N-hydroxysuccinimide (NHS) ester group of biotin-NHS creating a covalent linkage between the substrate and biotin. Referring to FIG. 5, the substrate 301 coated with biotin 302 localizes the streptavidin-adsorbed CNTs 401 to the cathode surface. Each streptavidin protein has four binding sites for biotin. The interaction of this binding pair results in extremely tight binding affinity, $Kd=10^{-14}$ (Savage et al., 1992, *Avidin-Biotin Chemistry: A Handbook*, Rockford, Ill.: Pierce Chemical Company).

Figure 6:
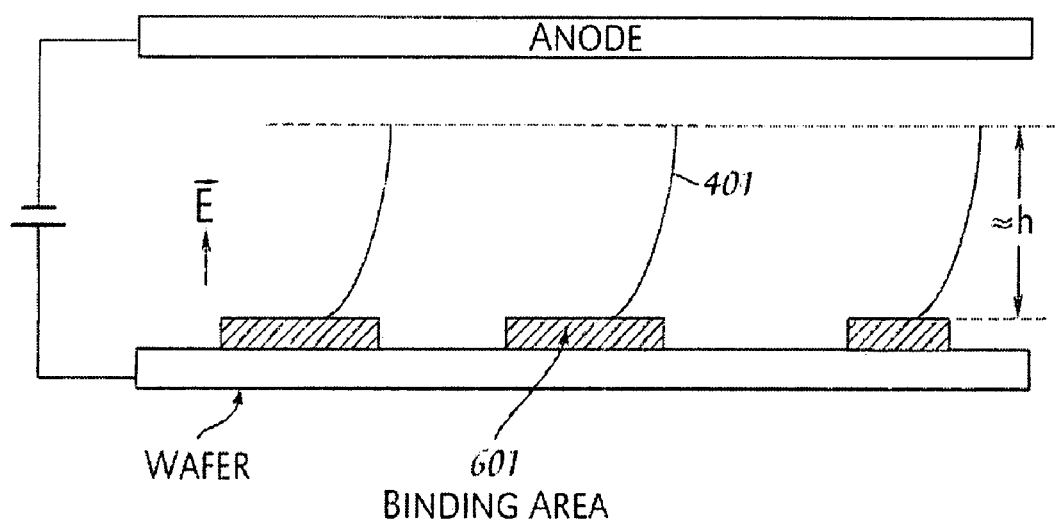
FIG. 6 illustrates a field emission device.

At this stage, the functionalized CNTs are deposited on the cathode substrate. Due to the strong specific binding between streptavidin and biotin, all the CNTs that were functionalized with streptavidin will bind to the substrate while all the CNTs not functionalized with streptavidin will not be bound to the substrate and will be washed off as shown in FIG. 5. Here, height h is defined and controlled by the depth of precise wafer insertion into the functionalizing agent (e.g., streptavidin), and is effectively uniform across the population of CNTs harvested from the wafer. The functionalized area of the free-end region of the CNTs is variable due to the variable native length of the CNTs as grown on the wafer. This variable functionalized region will adhere to the surface (e.g., at biotin layer), leaving h available to bend in the electric field toward the anode, as depicted in FIG. 6. Here, the streptavidin-biotin linkage 601 is depicted as a simplified rectangle on the surface of the substrate. The rectangle 601 illustrates the variable area of binding between the CNT 401 and the biotin layer. FIG. 6 also illustrates how a field emission device, such as a display, may be created. A phosphor (not shown) may be added to the anode.

Alternatively, the biotin-streptavidin linkage may be reversed in this process so that the streptavidin is on the second substrate in FIG. 4.

Figure 7:
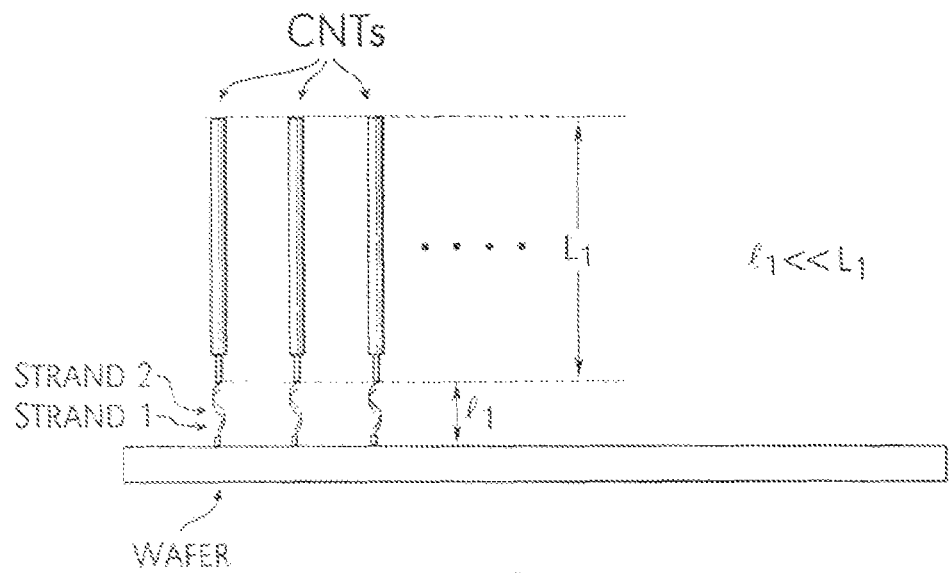
FIG. 7 illustrates DNA utilized to bind CNTs to a substrate.

Referring to FIG. 7, this process can be modified, for example by using complementary strands of short deoxyribonucleic acid (DNA) oligomers. One single-stranded oligomer (Strand 1) is covalently attached to the cathode surface using numerous available chemistries including but not limited to disulfide bonding, esterification, or amidation. DNA oligomers, generally of length less than 100 nucleotides, can be designed with assorted 3' or 5' end-modifications that allow for covalent attachment to surfaces, for example a 5' amine (NH2) terminus. If the substrate is derivatized with a carboxyl(COOH)-terminated silane, a condensation reaction will covalently link the DNA oligomer to the surface through an amide bond. The ability of each derivatized surface to attach nucleic acid oligomers varies, depending on the functional groups and the attachment condition. The chemistries of these interactions can be exploited following well-established genetic microarray and biosensor techniques (Beier and Hoheisel, Versatile derivatization of solid support media for covalent bonding on DNA-microchips, Nucleic Acids Research, Vol. 27, pp. 1970-1977). This strand can even be patterned on the cathode if needed by DNA microarray printing techniques which utilize automated micro-volume printers to achieve high-density gridded arrays of DNA or similar biological material; mask fabrication which can control patterning of an e-beam deposited oxide to protect specified regions from DNA or biotin conjugation; or other method. The complementary "sequence" oligomer (Strand 2) is covalently attached specifically to the CNT terminus by "precise insertion" method by the process described in FIG. 2, where the functionalizing solution is DNA oligomer. For example, the CNTs can be carboxyl-functionalized (CNT-COOH) by acid treatment via precise insertion described here in $H_2SO_4$—$HNO_3$ solution or commercially purchased as-modified. The $NH_2$-terminated DNA can be covalently linked to the CNT-COOH by condensation reaction, resulting in CNT-Strand 2 complexes. The DNA Strand 2 functionalized CNTs can now be localized to the Strand 1 derivatized cathode by the inherent annealing of complementary nucleic acid strands. In this case, the length of the double-stranded DNA complex is on the nanometer scale, while the CNT itself is microns in length.

Figure 8:
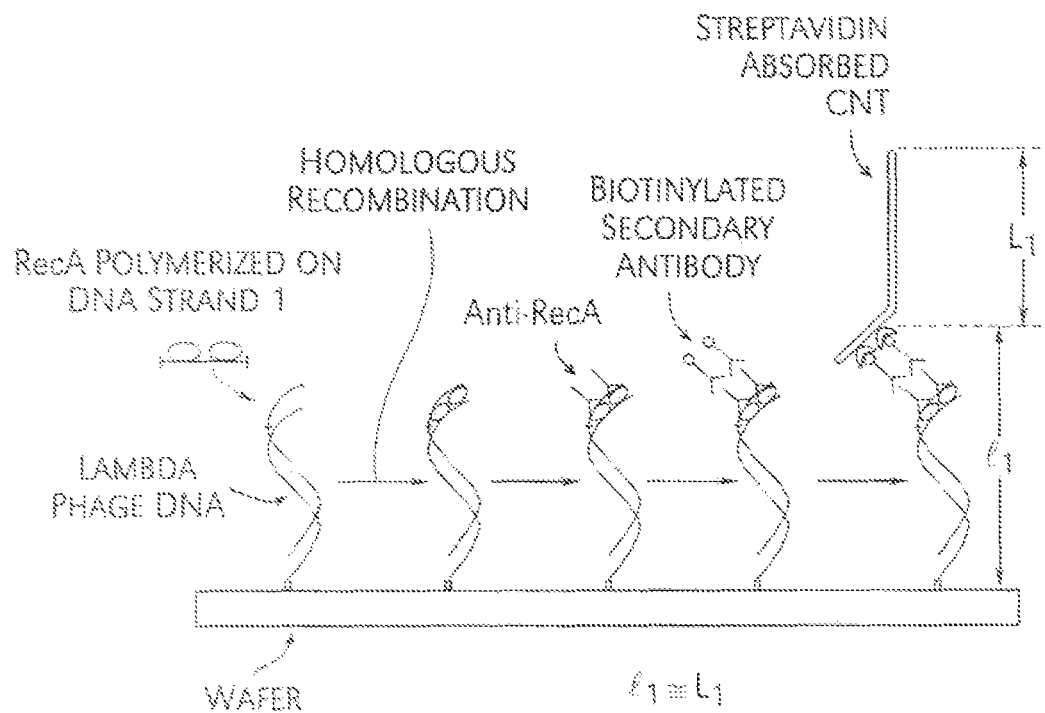
FIG. 8 illustrates another embodiment of the present invention.

Referring to FIG. 8, an alternate mechanism using long DNA may be designed using homologous DNA recombination via the RecA protein, as partially described by Erez Braun and associates (Braun et al., DNA-Templated Carbon Nanotube Field-Effect Transistor, Science, Vol. 302, Nov. 21, 2003). In this scenario, a single-stranded DNA (ssDNA) on the order of hundreds of nucleotides in length corresponding to the terminal sequence of the lambda phage genome is generated by polymerase chain reaction (PCR). This PCR fragment is polymerized with the RecA protein. RecA functions to homologously recombine ssDNA with complementary double-stranded DNA (dsDNA). In a separate reaction, linear double-stranded lambda phage genome is covalently attached to the cathode surface through standard surface chemistry, examples of which are described above. The RecA polymerized ssDNA is incubated with the ds-lambda-DNA-derivatized cathode and homologous recombination occurs, mediated by RecA. Now the RecA resides with the dsDNA complex on the cathode surface. Next, anti-RecA antibody is added to the cathode-dsDNA-RecA complex. The anti-RecA antibody binds RecA. A biotinylated secondary antibody (e.g., commercially available anti-mouse, anti-rabbit, etc.) is then added to the cathode complex which binds specifically to the anti-RecA antibody. Streptavidin-adsorbed CNTs (as in FIG. 2) are then localized to the cathode via the biotin moiety, and the process continues accordingly. In this case, the length of the double-stranded DNA-antibody complex is similar to the CNT itself. These materials are examples and there are many other possibilities depending on the adherence of the chemical layers to the cathode substrate and the strength of the binding between the functionalized CNTs and the intermediate layers.

Although the present invention and its advantages have been described in detail, it should be understood that various changes, substitutions and alterations can be made herein without departing from the spirit and scope of the invention as defined by the appended claims.

The invention claimed is:

1. A method comprising:
partially immersing carbon nanotubes (CNTs) on a first substrate in a biological solution to functionalize along only parts of the lengths of the CNTs with a biological molecule, wherein a variability in length of the functionalized parts of the lengths of the CNTs is greater than a variability in length of remainders of the lengths of the CNTs;
harvesting the functionalized CNTs from the first substrate;
functionalizing a second substrate with a complementary biological modification, which is a complementary binding partner to the biological molecule functionalizing along the parts of the lengths of the CNTs; and;
attaching the functionalized parts of the lengths of the CNTs to the complementary biological modification functionalizing the second substrate.

2. The method as recited in claim 1, wherein the biological solution comprises DNA.

3. The method as recited in claim 2, wherein the complementary biological modification comprises DNA.

4. The method as recited in claim 1, wherein the parts of the CNTs on the first substrate have varying lengths, and only parts of the lengths of CNTs having at least a predetermined length are functionalized with the biological molecule.

5. The method as recited in claim 1, further comprising:
positioning an anode a predetermined distance from the second substrate with the attached functionalized CNTs.

6. The method as recited in claim 1, wherein the variability in length of the functionalized parts of the lengths of the CNTs is characteristic of a process by which the CNTs were grown.

7. The method as recited in claim 1, wherein partially immersing CNTs comprises functionalizing sidewalls of the parts of the lengths of the CNTs with the biological molecule.

8. The method as recited in claim 1, further comprising growing the CNTs on the first substrate.

9. The method as recited in claim 1, wherein attaching the functionalized parts of the lengths of the CNTs to the complementary biological modification leaves the remainders of the lengths of the CNTs available to bend in an electric field of a field emission device.

10. The method as recited in claim 1, wherein partially immersing the CNTs comprises:
holding the first substrate above a biological solution; and
lowering the first substrate toward the biological solution.

11. A method comprising:
partially immersing carbon nanotubes (CNTs) in a biological solution to functionalize a biological molecule along only parts of the lengths of the CNTs, wherein the functionalized CNTs are attached to a first substrate, wherein a variability in length of the functionalized parts of the lengths of the CNTs is greater than a variability in length of remainders of the lengths of the CNTs;
harvesting the functionalized CNTs from the first substrate;
functionalizing a second substrate with a complementary biological modification that is a complementary binding partner to the biological molecule; and
attaching the harvested functionalized CNTs to the second substrate by binding the biological molecule to the complementary biological modification.

12. The method as recited in claim 11, further comprising growing the CNTs on the first substrate.

13. The method as recited in claim 11, wherein attaching the functionalized parts of the lengths of the CNTs to the complementary biological modification leaves the remainders of the lengths of the CNTs available to bend in an electric field of a field emission device.

14. The method as recited in claim 11, wherein partially immersing the CNTs comprises:
holding the first substrate above a biological solution; and
lowering the first substrate toward the biological solution.

15. The method as recited in claim 11, further comprising positioning an anode a predetermined distance from the second substrate with the attached functionalized CNTs.

16. The method as recited in claim 11, wherein attaching the harvested functionalized CNTs leaves remainders of the lengths of the CNTs available to bend in an electric field of a field emission device.

* * * * *